(12) United States Patent
Brandenburg

(10) Patent No.: US 8,633,164 B2
(45) Date of Patent: Jan. 21, 2014

(54) ANTIMICROBIAL PEPTIDES

(75) Inventor: Klaus Brandenburg, Hamburg (DE)

(73) Assignee: Forschungzentrum Borstel—Liebnizzentrum fur Medizin und Biowissenschaften, Borstel (DE)

( * ) Notice: Subject to any disclaimer, the term of this patent is extended or adjusted under 35 U.S.C. 154(b) by 302 days.

(21) Appl. No.: 12/936,976

(22) PCT Filed: Apr. 7, 2009

(86) PCT No.: PCT/EP2009/002565
§ 371 (c)(1),
(2), (4) Date: Jan. 10, 2011

(87) PCT Pub. No.: WO2009/124721
PCT Pub. Date: Oct. 15, 2009

(65) Prior Publication Data
US 2011/0105416 A1    May 5, 2011

(30) Foreign Application Priority Data

Apr. 9, 2008    (EP) .................................... 08007064

(51) Int. Cl.
| A61K 38/16 | (2006.01) |
| A61K 38/10 | (2006.01) |
| C07H 21/04 | (2006.01) |
| C12N 15/63 | (2006.01) |
| C12N 1/20 | (2006.01) |
| C12P 21/02 | (2006.01) |
| C12P 21/00 | (2006.01) |
| A61P 31/04 | (2006.01) |
| A61P 31/12 | (2006.01) |
| C12N 1/19 | (2006.01) |
| C12N 5/10 | (2006.01) |

(52) U.S. Cl.
USPC ....... 514/21.4; 530/326; 530/324; 435/320.1; 435/252.3; 435/69.1; 435/69.7; 435/254.2; 435/325; 536/23.1

(58) Field of Classification Search
None
See application file for complete search history.

(56) References Cited

U.S. PATENT DOCUMENTS 6,191,114 B1 * 2/2001 Vallespi et al. ................. 514/3.7
6,384,188 B1 * 5/2002 Hoess et al. ................... 530/326

FOREIGN PATENT DOCUMENTS

| EP | 0 905 141 | 3/1999 |
| EP | 1992638 A1 * | 11/2008 |
| WO | WO 95/05393 | 2/1995 |
| WO | WO 2007/095867 | 8/2007 |

OTHER PUBLICATIONS

International Search Report for international Application No. PCT/EP2009/002565 mailed Aug. 28, 2009.

* cited by examiner

*Primary Examiner* — Cecilia J Tsang
*Assistant Examiner* — Tara Martinez
(74) *Attorney, Agent, or Firm* — Hunton & Williams LLP

(57) ABSTRACT

The present invention relates to a peptide of linear, non-cyclic structure consisting of or comprising 17 to 23 amino acids, wherein the amino acids in positions 1 to 23, counted from the N-terminus, are as follows (1) G, S or lacking; (2) C or lacking; (3) K or R; (4) K or R; (5) Y, W or F; (6) K or R; (7) K or R; (8) F, W or L; (9) K or R; (10) K or L or lacking; (11) W, L or F; (12) K or R; (13) F, Y or C; (14) K or R; (15) G or Q; (16) K or R; (17) F, L or W; (18) F or W; (19) F, L or W; (20) W or F; (21) C or lacking; (22) F or G or lacking (23) G or lacking. Further, the invention relates to a nucleic acid molecule encoding the peptide of the invention, an expression vector comprising the nucleic acid molecule of the invention, a host cell which may be grown in cell culture comprising the vector of the invention, and a method of producing the peptide of the invention comprising culturing the host cell of the invention and collecting the peptide produced. Also, the present invention relates to a pharmaceutical composition comprising the peptide of the invention, the peptide produced by the method of the invention, the nucleic acid molecule of the invention, the expression vector of the invention or the host cell of the invention and a kit comprising the peptide of the invention, the peptide produced by the method of the invention, the nucleic acid molecule of the invention, the expression vector of the invention or the host cell of the invention.

14 Claims, 8 Drawing Sheets

A

B

SEQUENCE LISTING

<160> NUMBER OF SEQ ID NOS: 15

<210> SEQ ID NO 1
<211> LENGTH: 17
<212> TYPE: PRT
<213> ORGANISM: Artificial Sequence
<220> FEATURE:
<223> OTHER INFORMATION: Synthetic antimicrobial peptide 1Pep17-1

<400> SEQUENCE: 1

Lys Lys Phe Arg Arg Leu Lys Trp Lys Tyr Lys Gly Lys Phe Trp Phe
1               5                   10                  15

Trp

<210> SEQ ID NO 2

-continued

```
<211> LENGTH: 17
<212> TYPE: PRT
<213> ORGANISM: Artificial Sequence
<220> FEATURE:
<223> OTHER INFORMATION: Synthetic antimicrobial peptide 1Pep17-2

<400> SEQUENCE: 2

Lys Lys Tyr Arg Arg Phe Arg Trp Lys Phe Lys Gly Lys Phe Trp Phe
1               5                   10                  15

Trp

<210> SEQ ID NO 3
<211> LENGTH: 17
<212> TYPE: PRT
<213> ORGANISM: Artificial Sequence
<220> FEATURE:
<223> OTHER INFORMATION: Synthetic antimicrobial peptide 1Pep17-3

<400> SEQUENCE: 3

Arg Arg Tyr Lys Lys Phe Lys Trp Arg Tyr Gly Arg Phe Trp Phe
1               5                   10                  15

Trp

<210> SEQ ID NO 4
<211> LENGTH: 21
<212> TYPE: PRT
<213> ORGANISM: Artificial Sequence
<220> FEATURE:
<223> OTHER INFORMATION: Synthetic antimicrobial peptide 1Pep19-1

<400> SEQUENCE: 4

Gly Cys Lys Lys Phe Arg Arg Leu Lys Trp Lys Tyr Lys Gly Lys Phe
1               5                   10                  15

Trp Phe Trp Cys Gly
            20

<210> SEQ ID NO 5
<211> LENGTH: 21
<212> TYPE: PRT
<213> ORGANISM: Artificial Sequence
<220> FEATURE:
<223> OTHER INFORMATION: Synthetic antimicrobial peptide 1Pep19-2

<400> SEQUENCE: 5

Gly Cys Lys Lys Tyr Arg Arg Phe Arg Trp Lys Phe Lys Gly Lys Phe
1               5                   10                  15

Trp Phe Trp Cys Gly
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic antimicrobial peptide 1Pep19-3

<400> SEQUENCE: 6

Gly Cys Arg Arg Tyr Lys Lys Phe Lys Trp Arg Tyr Arg Gly Arg Phe
1               5                   10                  15

Trp Phe Trp Cys Gly
            20

<210> SEQ ID NO 7
<211> LENGTH: 19
<212> TYPE: PRT
```

```
<213> ORGANISM: artificial sequence
<220> FEATURE:
<223> OTHER INFORMATION: Synthetic antimicrobial peptide 1Pep19-4

<400> SEQUENCE: 7

Gly Lys Lys Tyr Arg Arg Phe Arg Trp Lys Phe Lys Gly Lys Trp Phe
1               5                   10                  15

Trp Phe Gly

<210> SEQ ID NO 8
<211> LENGTH: 19
<212> TYPE: PRT
<213> ORGANISM: Artificial Sequence 1Pep19-5
<220> FEATURE:
<223> OTHER INFORMATION: Synthetic antimicrobial peptide

<400> SEQUENCE: 8

Gly Lys Lys Tyr Arg Arg Phe Arg Trp Lys Phe Arg Gly Arg Phe Trp
1               5                   10                  15

Phe Trp Gly

<210> SEQ ID NO 9
<211> LENGTH: 21
<212> TYPE: PRT
<213> ORGANISM: Artificial Sequence
<220> FEATURE:
<223> OTHER INFORMATION: Synthetic antimicrobial peptide 1Pep19-6

<400> SEQUENCE: 9

Gly Cys Lys Lys Phe Arg Arg Phe Lys Leu Lys Cys Lys Gln Lys Leu
1               5                   10                  15

Trp Leu Trp Cys Gly
            20

<210> SEQ ID NO 10
<211> LENGTH: 18
<212> TYPE: PRT
<213> ORGANISM: Artificial Sequence
<220> FEATURE:
<223> OTHER INFORMATION: Synthetic antimicrobial peptide 1Pep19-7

<400> SEQUENCE: 10

Gly Lys Lys Tyr Arg Arg Phe Trp Lys Phe Lys Gly Lys Trp Phe Phe
1               5                   10                  15

Trp Gly

<210> SEQ ID NO 11
<211> LENGTH: 19
<212> TYPE: PRT
<213> ORGANISM: Artificial Sequence
<220> FEATURE:
<223> OTHER INFORMATION: Synthetic antimicrobial peptide 1Pep19-8

<400> SEQUENCE: 11

Gly Arg Arg Tyr Lys Lys Phe Arg Trp Lys Phe Lys Gly Arg Trp Phe
1               5                   10                  15

Trp Phe Gly

<210> SEQ ID NO 12
<211> LENGTH: 21
<212> TYPE: PRT
<213> ORGANISM: Artificial Sequence
<220> FEATURE:
<223> OTHER INFORMATION: Synthetic antimicrobial peptide 1Pep19-9
```

```
<400> SEQUENCE: 12

Gly Cys Arg Arg Phe Lys Lys Phe Arg Trp Lys Tyr Lys Gly Lys Phe
1               5                   10                  15

Trp Phe Trp Cys Gly
            20

<210> SEQ ID NO 13
<211> LENGTH: 19
<212> TYPE: PRT
<213> ORGANISM: Artificial Sequence
<220> FEATURE:
<223> OTHER INFORMATION: Synthetic antimicrobial peptide lPep19-10

<400> SEQUENCE: 13

Gly Arg Arg Tyr Lys Lys Phe Lys Trp Arg Phe Arg Gly Arg Phe Trp
1               5                   10                  15

Phe Trp Gly

<210> SEQ ID NO 14
<211> LENGTH: 21
<212> TYPE: PRT
<213> ORGANISM: Artificial Sequence
<220> FEATURE:
<223> OTHER INFORMATION: Synthetic antimicrobial peptide lPep19-11

<400> SEQUENCE: 14

Gly Cys Arg Arg Trp Lys Lys Phe Arg Trp Arg Tyr Arg Gly Lys Phe
1               5                   10                  15

Trp Phe Trp Cys Gly
            20

<210> SEQ ID NO 15
<211> LENGTH: 23
<212> TYPE: PRT
<213> ORGANISM: Artificial Sequence
<220> FEATURE:
<223> OTHER INFORMATION: Synthetic antimicrobial peptide lPep19-12

<400> SEQUENCE: 15

Gly Cys Arg Arg Phe Lys Lys Phe Lys Lys Trp Arg Tyr Arg Gly Arg
1               5                   10                  15

Phe Trp Phe Trp Cys Phe Gly
            20
```

US 8,633,164 B2

ANTIMICROBIAL PEPTIDES

CROSS-REFERENCE TO RELATED APPLICATIONS

Figure 1:
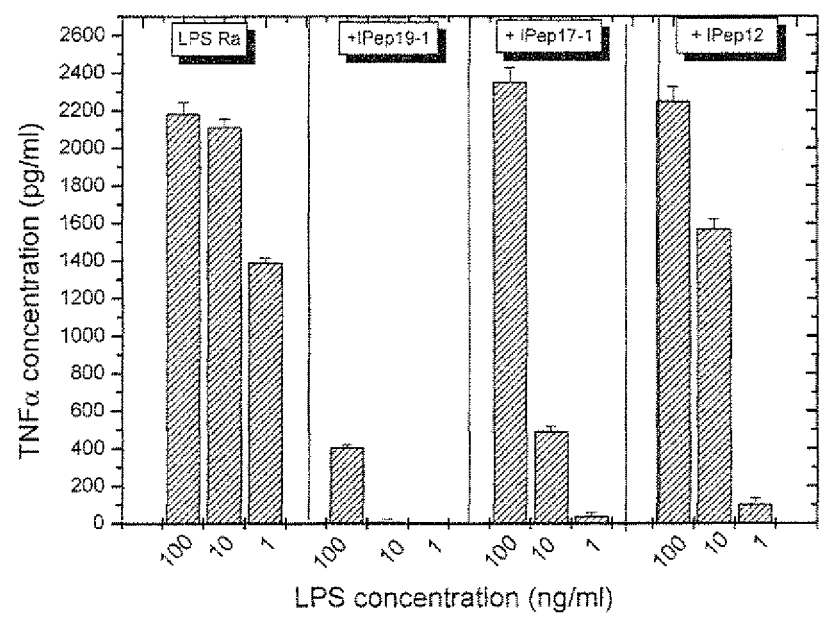

This application is the U.S. National Stage application of International Application No. PCT/EP2009/002565, filed Apr. 7, 2009, which claims priority to EP 08007064.2, filed Apr. 9, 2008, the disclosure of which is hereby incorporated by reference.

BACKGROUND OF THE INVENTION (i) Field of the Invention:

The present invention relates to a peptide of linear, non-cyclic structure consisting of or comprising 17 to 23 amino acids, wherein the amino acids in positions 1 to 23, counted from the N-terminus, are as follows (1) G, S or lacking; (2) C or lacking; (3) K or R; (4) K or R; (5) Y, W or F; (6) K or R; (7) K or R; (8) F, W or L; (9) K or R; (10) K or L or lacking; (11) W, L or F; (12) K or R; (13) F, Y or C; (14) K or R; (15) G or Q; (16) K or R; (17) F, L or W; (18) F or W; (19) F, L or W; (20) W or F; (21) C or lacking; (22) F or G or lacking (23) G or lacking. Further, the invention relates to a nucleic acid molecule encoding the peptide of the invention, an expression vector comprising the nucleic acid molecule of the invention, a host cell which may be grown in cell culture comprising the vector of the invention, and a method of producing the peptide of the invention comprising culturing the host cell of the invention and collecting the peptide produced. Also, the present invention relates to a pharmaceutical composition comprising the peptide of the invention, the peptide produced by the method of the invention, the nucleic acid molecule of the invention, the expression vector of the invention or the host cell of the invention and a kit comprising the peptide of the invention, the peptide produced by the method of the invention, the nucleic acid molecule of the invention, the expression vector of the invention or the host cell of the invention.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

(ii) Description of the Related Art:

In Germany alone more than 60000 people per year die from bacterial blood poisoning (sepsis). A new approach to fight this and other conditions has been the use of synthetic antimicrobial peptides (AMPs) on the basis of particular motifs of human and other proteins, which bind to bacterial pathogenicity factors such as lipopolysaccharide (LPS). It is known that the latter molecules are to a considerable degree responsible for inflammation and infection.

The approach to use AMPs has gained some interests in the last years. Usually, AMPs are based on LPS-binding defense proteins such as lactoferrin, granulysins and cationic antimicrobial peptides (CAP) (Andersson et al., 1996, Garidel et al., 2007, Ramamoorthy et al., 2006, Vallespi et al., 2003). Most of these studies, however, concentrated on killing the infectious bacteria rather than neutralizing free LPS. The existence of isolated LPS, released from bacteria by the action of the immune system or simply by cell dividing, is one of the main problems in the anti-septic fight.

Some studies have used the LPS-binding domain of the LALF-protein (Hoess et al., 1993, Paus et al., 2002), and have synthesized linear and cyclic peptides, with which it was possible to obtain a certain LPS-neutralization in vitro, but also in vivo, e.g. in a mouse model of endotoxicity (Dankesreiter et al., 2000, Garidel et al., 2007, Hoess et al., 1993, Leslie et al., 2006, More et al., 2006, Ried et al., 1996, Vallespi et al., 2003). It was found that some of these peptides have a sufficient half life in serum. However, the question of whether these compounds suppress the endotoxicity effectively and are suitable as possible anti-sepsis agents remained unanswered.

Comprehensive biophysical studies were performed, in which the essential parameters important for LPS-neutralization by particular cyclic AMPs or peptides based on porcine NK-lysin or human granulysin could be characterized (Andrä et al., 2004, Andrä et al., 2007, Andrä et al., 2004, Andrä et al., 2004, Andrä et al., 2007, Chen et al., 2007). Among these parameters are surface potential of the LPS head group, the fluidity of the lipid A acyl chains, the lipid A aggregate structure, and the incorporation into phospholipid liposomes in the absence and the presence of the LPS-binding protein LBP.

It was found that the LPS-neutralization by these AMPs was not sufficiently high to use them in animal experiments. The problem to obtain suitable AMP compounds is a severe problem due to the extremely high number of combination possible starting from the 20 proteinogenic amino acids. An approach to develop suitable AMP must include their ability to act antimicrobially as well as to neutralize LPS. For this, a detailed knowledge of the size, conformation, and aggregate structure of LPS/lipid A is necessary. Some of these parameters have been determined in previous reports (Brandenburg, 1993, Brandenburg et al., 1999, Brandenburg et al., 1990, Brandenburg et al., 1992, Brandenburg et al, 1997, Brandenburg et al., 2000, Brandenburg et al., 2002, Brandenburg et al., 1993, Brandenburg et al., 1998, Brandenburg et al., 1996), for a review see Brandenburg and Wiese, 2004.

However, even with this information available, there is still a need of providing peptides with excellent antimicrobial properties.

SUMMARY OF THE INVENTION

Accordingly the present invention relates to a peptide of linear, non-cyclic structure consisting of or comprising 17 to 23 amino acids, wherein the amino acids in positions 1 to 23, counted from the N-terminus, are as follows (1) G, S or lacking; (2) C or lacking; (3) K or R; (4) K or R; (5) Y, W or F; (6) K or R; (7) K or R; (8) F, W or L; (9) K or R; (10) K or L or lacking; (11) W, L or F; (12) K or R; (13) F, Y or C; (14) K or R; (15) G or Q; (16) K or R; (17) F, L or W; (18) F or W; (19) F, L or W; (20) W or F; (21) C or lacking; (22) F or G or lacking (23) G or lacking.

DETAILED DESCRIPTION OF THE INVENTION

The term "peptide" generally describes linear molecular chains of amino acids containing up to 30 amino acids covalently linked by peptide bonds. However, as defined above, the peptide of the invention consists of or comprises 17 to 23 amino acids. The total number of amino acids comprised in the peptide may increase to preferably up to 30 if one or more amino acids are added to peptides of 17 to 23 amino acids at their N- and/or C-terminus. Said amino acids may or may not contribute to the functionality of the peptide. In other words, amino acid(s) added may or may not confer a distinct function to the peptide, be it its antimicrobial or antiviral activity or another function.

The number of amino acids may further increase if the peptide of the invention is fused to another peptide or to a polypeptide (see below). Peptides may form oligomers consisting of at least two identical or different molecules. The corresponding higher order structures of such multimers are, correspondingly, termed homo- or heterodimers, homo- or heterotrimers etc.

The one-letter code abbreviations as used to identify amino acids throughout the present invention correspond to those commonly used for amino acids.

The peptide of the present invention can be produced synthetically. Chemical synthesis of peptides is well known in the art. Solid phase synthesis is commonly used and various commercial synthesizers are available, for example automated synthesizers by Applied Biosystems Inc., Foster City, Calif.; Beckman; MultiSyntech, Bochum, Germany etc. Solution phase synthetic methods may also be used, although they are less convenient. For example, peptide synthesis can be carried out using Nα-9-fluorenylmethoxycarbonyl amino acids and a preloaded trityl resin or an aminomethylated polystyrene resin with a p-carboxytritylalcohol linker. Couplings can be performed in dimethylformamide using N-hydroxybenzotriazole and 2-(1H-benzotriazole-1-yl)-1,1,3,3-tetramethyluronium hexafluorophosphate. Commonly used side chain protecting groups are tert-butyl for D, E and Y; trityl for N, Q, S and T; 2,2,4,6,7-pentamethyldihydroxybenzofruan-5-sulfonyl for R; and butyloxycarbonyl for K. After synthesis, the peptides are deprotected and cleaved from the polymer support by treatment with e.g. 92% trifluoracetic acid/4% triethylsilane/4% $H_2O$. The peptides can be precipitated by the addition of tert-butylether/pentane (8:2) and purified by reversed-phase HPLC. The peptides are commonly analysed by matrix-associated laser desorption time-of-flight mass spectrometry. By using these standard techniques, naturally occurring amino acids may be substituted with unnatural amino acids, particularly D-stereoisomers, and also with amino acids with side chains having different lengths or functionalities. Functional groups for conjugating to small molecules, label moieties, peptides, or proteins may be introduced into the molecule during chemical synthesis. In addition, small molecules and label moieties may be attached during the synthetic process. Preferably, introduction of the functional groups and conjugation to other molecules minimally affects the structure and function of the subject peptide.

The N- and C-terminus of the peptide as well as any amino acid comprised in the peptide apart from the terminal amino acids may be derivatized using conventional chemical synthetic methods. The peptides of the invention may contain an acyl group, such as an acetyl group. Methods for acylating, and specifically for acetylating the free amino group at the N-terminus are well known in the art. For the C-terminus, the carboxyl group may be modified by esterification with alcohols or amidated to form —$CONH_2$ or CONHR. Methods of esterification and amidation are well known in the art.

Furthermore, the peptide of the invention may also be produced semi-synthetically, for example by a combination of recombinant and synthetic production. In the case that fragments of the peptide are produced synthetically, the remaining part of the peptide would have to be produced otherwise, e.g. recombinantly as described further below, and then be linked to the fragment to form the peptide of the invention.

The present inventors have found peptides based on the LPS-binding domain of an animal LPS-binding protein from *Limulus polyphemus*, the *Limulus* anti-LPS factor (LALF) exerting a high antimicrobial activity. By optimal variation of the amino acid sequence of the original LALF domain it was possible to obtain peptides exerting a highly increased LPS neutralizing activity by binding to the lipid A part of LPS. In addition, it was surprisingly found that the peptides of the present invention also exert antiviral activity and/or may be applicable in cancer therapy.

As mentioned above, the peptide of the present invention exerts antimicrobial activity. In the context of the present invention, antimicrobial activity denotes the binding to and the resulting inhibition of bacterial LPS.

LPS is a major component of the outer membrane of Gram-negative bacteria, contributing greatly to the structural integrity of the bacteria, and protecting the membrane from certain kinds of chemical attack. LPS is an endotoxin, and induces a strong response from normal animal immune systems. The only Gram-positive bacteria that possesses LPS is *Listeria monocytogenes*, the common infective agent in unpasteurized milk.

LPS acts as the prototypical endotoxin, because it binds the CD14/TLR4/MD2 receptor complex, which promotes the secretion of pro-inflammatory cytokines in many cell types, but especially in macrophages. An "LPS challenge" in immunology is the exposing of the subject to an LPS which may act as a toxin. LPS also increases the negative charge of the cell membrane and helps stabilize the overall membrane structure. LPS comprises three parts: polysaccharide (O) side chains, core polysaccharide (core oligosaccharide in genus *Neisseria*) and lipid A. The polysaccharide side chain is referred to as the O-antigen of the bacteria. O side chain (O-antigen) is also a polysaccharide chain that extends from the core polysaccharide. The composition of the O side chain varies between different Gram-negative bacterial strains. The presence or absence of O chains determine whether the LPS is considered rough or smooth. Full length O-chains would render the LPS smooth while the absence or reduction of O-chains would make the LPS rough. Bacteria with rough LPS usually have more penetrable cell membranes to hydrophobic antibiotics since a rough LPS is more hydrophobic. O side chains are easily recognized by the antibodies of the host, however, the nature of the chain can easily be modified by Gram-negative bacteria to avoid detection. Core oligosaccharide contains unusual sugars (e.g. KDO, keto-deoxyoctulonate and heptose). The core oligosaccharide is attached to lipid A. Lipid A contains unusual fatty acids (e.g. hydroxymyristic acid) and is embedded into the outer membrane while the rest of the LPS projects from the surface. Lipid A is the bioactive moiety of LPS responsible for all toxic properties. Accordingly, binding to lipid A is a prerequisite for the inactivation of LPS as pathogenicity factor. Furthermore, due to the highly positive charge of the AMPs of the present invention, these are also able to kill Gram-negative and Gram-positive bacteria, because, in contrast to mammalian cells, the surface of bacterial membranes have a strong negative charge density.

Thus, the term "anitimicrobial activity" refers to said activity in bacteria which express LPS, i.e. gram-negative bacteria. Methods of testing peptides for said antimicrobial activity are known in the art and described in the appended examples. The evaluation of the antimicrobial activity of a peptide can be done by determining its minimum inhibitory concentration (MIC) and minimum bactericidal concentration (MBC) against a collection of Gram-negative bacterial strains. These strains include extended-spectrum beta-lactamase (ESBL) *E. coli* (n=2), as well as bacterial strains either resistant to cationic peptides (*Yersinia pestis* (n=1), *Proteus mirabilis* (n=1)

and *Brucella abortus* (n=1)) or multiresistant to conventional antibiotics (*Shigella sonnei* (n=1), *Klebsiella oxytoca* (n=1), *Acinetobacter baumannii* (n=1), and *Stenotrophomonas maltophilia* (n=1)) *Burkholderia cepacia* (n=1). Additionally, the susceptibility of mucosal pathogens (*Haemophilus influenzae* (n=1), *Neisseria meningitidis* (n=1), *Bordetella bronchiseptica* (n=1)) can be characterized. MIC and MBC of the peptides will be determined by the broth microdilution test in divalent cation adjusted Mueller Hinton medium according to Clinical and Laboratory Standard Institute (CLSI; formerly NCCLS) guidelines (NCCLS, 2000, *Approved Standard: M7-A5*). Preferred concentrations of the peptide of the present invention to be applied in order to exert its antimicrobial activity are 10 to 20 µg/ml.

In the course of the present invention, the present inventors found that a suitable amino acid sequence to neutralize LPS must obey several criteria: It must have a sufficient amount of positively charged amino acids such as arginin (R) and lysin (K), some hydrophobic amino acids such as tryptophan (W) and phenylalanin (F), but also tyrosin (Y) and, to a certain extent, cystein (C), and a sufficiently flexible chain of 'correct' length. Preferably, the number of positively charged amino acids ranges from 7 to 9. It is also preferred that the number of hydrophobic amino acids is 7 or 8. The remaining amino acids are preferably polar.

The peptides of the invention preferably have a length of 17 to 23 amino acids in order to be able to effectively bind to the lipid A domain of LPS but may also comprise further amino acids at their termini as described above. They consist of three regions or domains: The N-terminal is predominantly negatively charged, the C-terminal predominantly hydrophobic and the central region is composed of amino acids belonging to different classes. There is experimental evidence that the N-terminal binds to the 1-phosphate of the lipid A-moiety of LPS, the central region binds to the 4'-phosphate, while the hydrophobic C-terminal inserts into the hydrophobic moiety of lipid A.

Several experiments were performed in order to test the approach used in the present invention and the peptides found.

Figure 2:
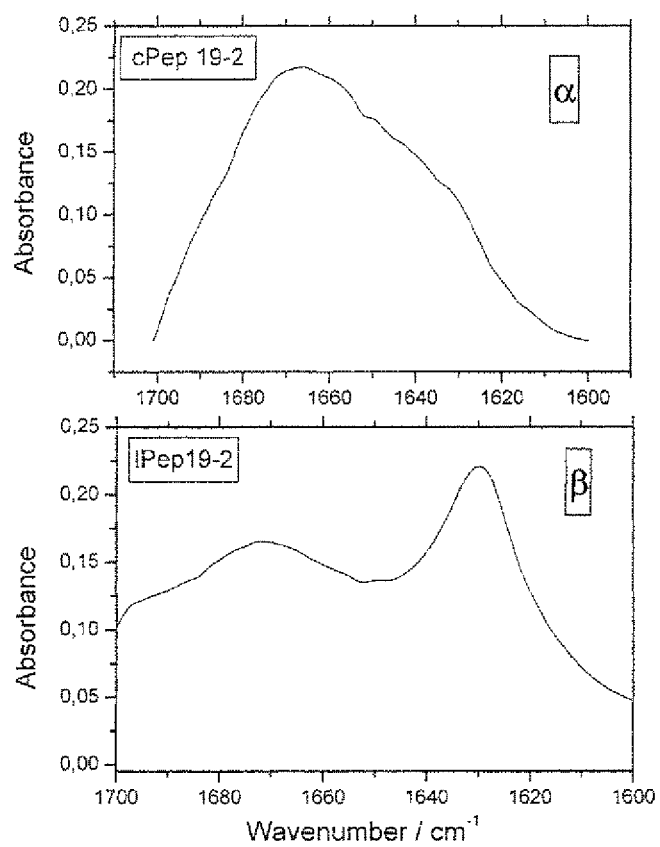

It was found that the shortening of the peptide length resulted in a decrease of the inhibition of the LPS-induced cytokine expression (see FIG. 1). Furthermore, it was found that the cyclisation of peptides, obtained by S—S— binding via cysteine residues, resulted in a significantly reduced inhibition of cytokine production indicating a lower activity. The reason for this seems to lie in the secondary structures of the peptides. All highly active AMPs have a predominant β-sheet structure, while the corresponding cyclic compound essentially folds into an α-helix, as is shown in the evaluation of the amide I-vibration in FTIR experiments (FIG. 2).

Figure 3:
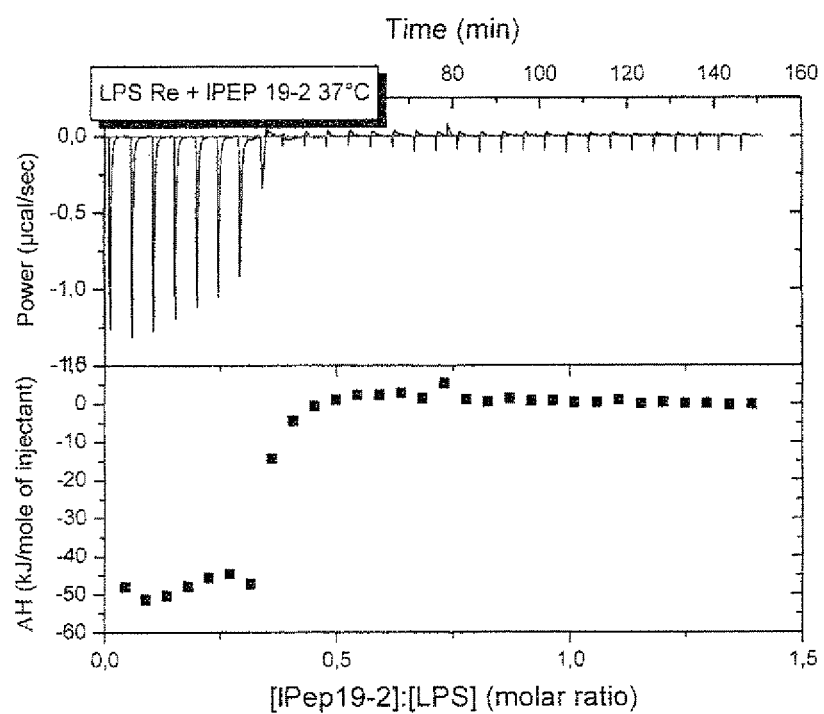

The binding stoichiometry of the highly active IPep19-2 was investigated exemplarily with isothermal titration calorimetry. The peptide exhibited very strong binding to LPS with saturation already at a molar ratio [LPS]:[IPep19-2] of 3:1 (FIG. 3).

Figure 4:
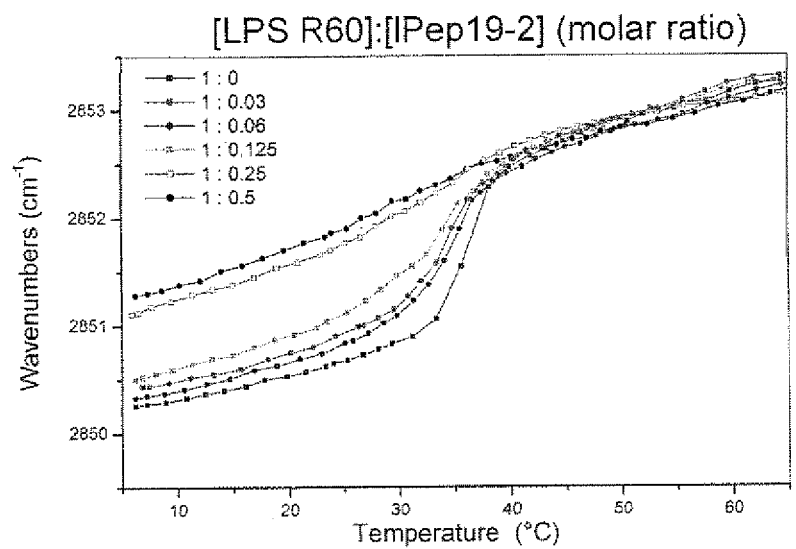
Figure 4:
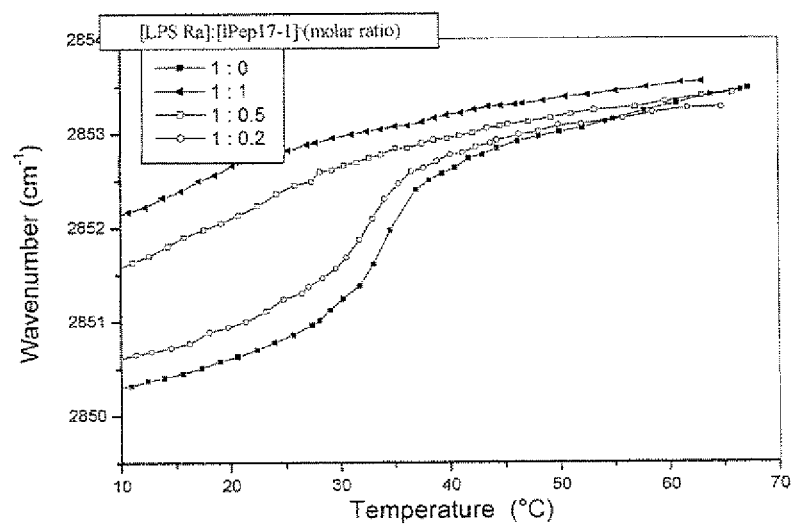

As a further example of a strongly binding peptide, the influence of IPep17-1 on the gel to liquid crystalline phase transition of the hydrocarbon chains of LPS is shown (FIG. 4). As can be seen, the wavelengths of the peak position of the symmetric stretching vibration of the methylene groups strongly increase at all temperatures. This correponds to a a drastic fluidization of the acyl chain moiety of LPS induced by the peptide which is comparable to that caused by the 'gold standard' polymyxin B (PMB). It should be noted that although PMB is a very good AMP and is able to suppress many LPS-induced activities, it is not suitable as systemic medicament due to its inherent toxicity.

Figure 5:
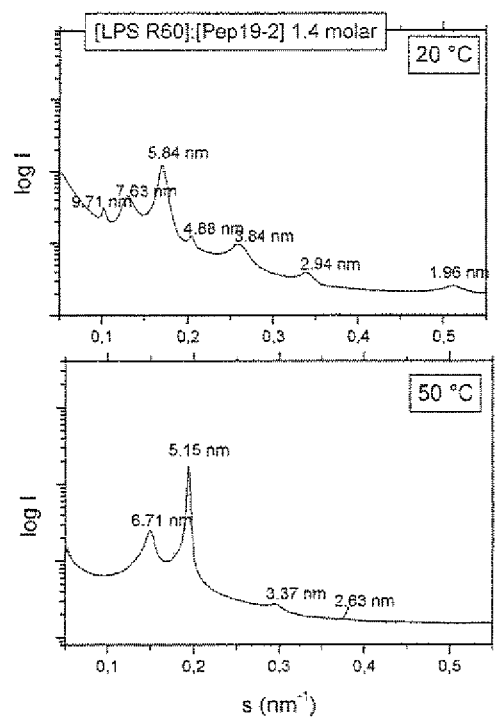

As example of the influence of the peptides on the aggregate structures of LPS, small-angle X-ray scattering data for the LPS:Pep19-2 complex are shown (FIG. 5). At 20° C. the data are indictive for the existence of multilamellar aggregates with periodicities at 9.71, 7.63, and 5.84 nm (the reflections at 4.88, 3.84, and 2.94 nm correspond to the second order), at, 50° C. only two periodicities at 6.71 and 5.15 nm are found. The multilamellarisation of LPS, a necessary prerequisite for its inactivation, and the periodicities values are clearly a proof for extremely densely packed aggregates, thus explaining the LPS neutralization.

Figure 6:
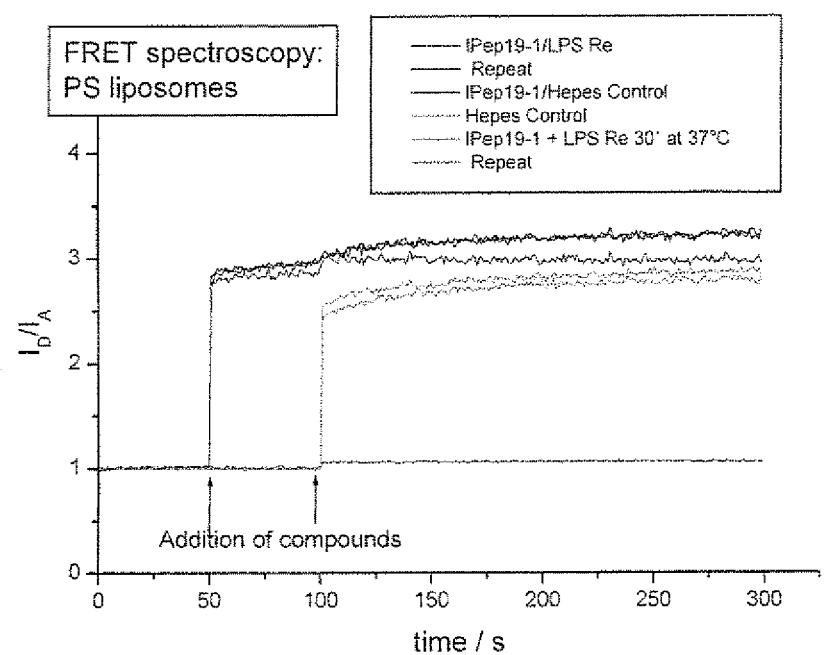

Furthermore, in fluorescence resonance energy transfer measurements with labelled negatively charged phosphatidylserine liposomes, it could be shown that the antimicrobial peptides of the invention incorporate into the liposomes in the absence as well as the presence of LPS (FIG. 6).

Figure 7:
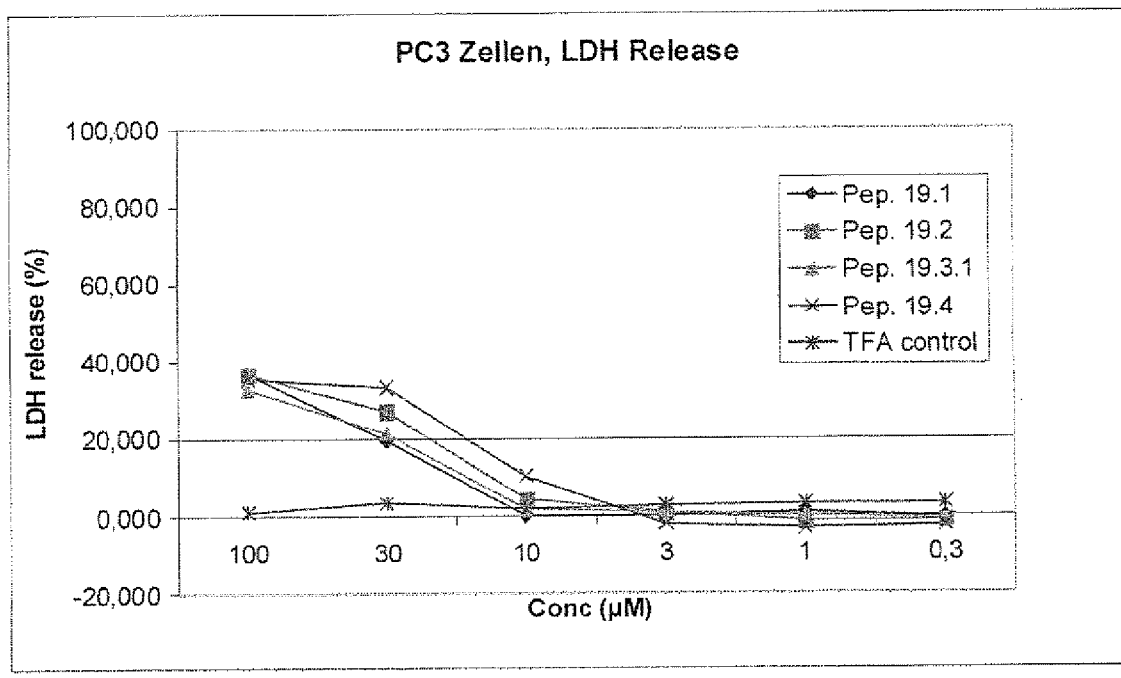

From FIG. 7, it can be seen that cell damage to the cancer cell line PC3 increases with increasing concentrations of peptide thus demonstrating the applicability of the peptides of the invention in cancer therapy.

Figure 8:
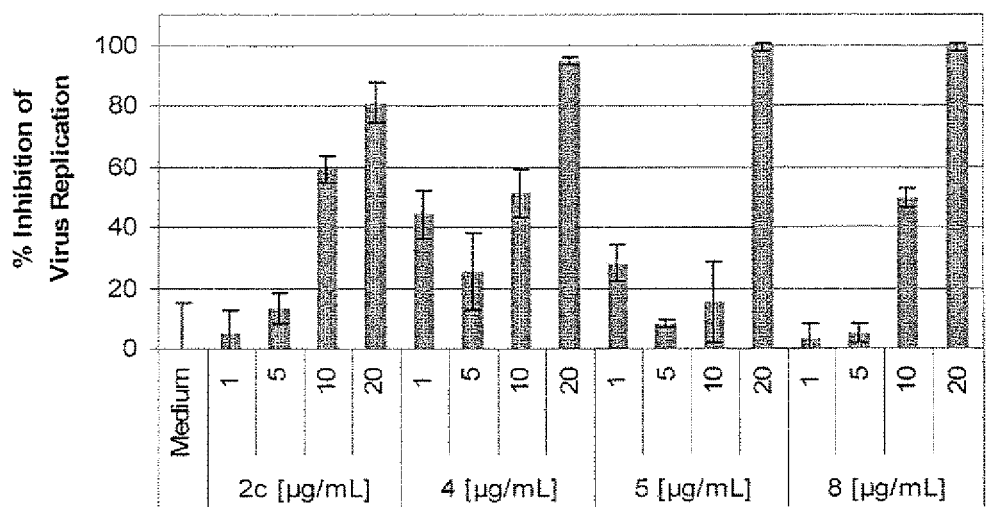

Finally, FIG. 8 demonstrates that the peptides of the invention exert antiviral activity resulting in an inhibition of virus replication of up to 99% in a T-cell line.

In summary, the present inventors unexpectedly found a formula for peptides having antimicrobial and antiviral activity and suitable for the treatment of infectious diseases or cancer.

In a preferred embodiment, the peptide consists of 17 to 23 amino acids.

In another preferred embodiment, the peptide consists of 17 to 21 amino acids, wherein the amino acids in positions 1 to 21, counted from the N-terminus, are as follows (1) G, S or lacking; (2) C or lacking; (3) K or R; (4) K or R; (5) Y or F; (6) K or R; (7) K or R; (8) F, W or L; (9) K or R; (10) W, L or F; (11) K or R; (12) F, Y or C; (13) K or R; (14) G or Q; (15) K or R; (16) F, L or W; (17) F or W; (18) F, L or W; (19) W or F; (20) C or lacking; (21) G or lacking.

In another preferred embodiment, the peptide of the invention has any one of the following amino acid sequences

| | (SEQ ID NO: 1) |
|---|---|
| lPep17-1: | KKFRRLKWKYKGKFWFW |

| | (SEQ ID NO: 2) |
|---|---|
| lPep17-2: | KKYRRFRWKFKGKFWFW |

| | (SEQ ID NO: 3) |
|---|---|
| lPep17-3: | RRYKKFKWRYRGRFWFW |

| | (SEQ ID NO: 4) |
|---|---|
| lPep19-1: | GCKKFRRLKWKYKGKFWFWCG |

| | (SEQ ID NO: 5) |
|---|---|
| lPep19-2: | GCKKYRRFRWKFKGKFWFWCG |

| | (SEQ ID NO: 6) |
|---|---|
| lPep19-3: | GCRRYKKFKWRYRGRFWFWCG |

| | (SEQ ID NO: 7) |
|---|---|
| lPep19-4: | GKKYRRFRWKFKGKWFWFG |

| | (SEQ ID NO: 8) |
|---|---|
| lPep19-5: | GKKYRRFRWKFRGRFWFWG |

| | (SEQ ID NO: 9) |
|---|---|
| lPep19-6: | GCKKFRRFKLKCKQKLWLWCG |

```
1Pep19-7:         GKKYRRFWKFKGKWFFWG
                                        (SEQ ID NO: 10)

1Pep19-8:         GRRYKKFRWKFKGRWFWFG
                                        (SEQ ID NO: 11)

1Pep19-9:         GCRRFKKFRWKYKGKFWFWCG
                                        (SEQ ID NO: 12)

1Pep19-10:        GRRYKKFKWRFRGRFWFWG
                                        (SEQ ID NO: 13)

1Pep19-11:        GCRRWKKFRWRYRGKFWFWCG
                                        (SEQ ID NO: 14)

1Pep19-12:        GCRRFKKFKKWRYRGRFWFWCFG.
                                        (SEQ ID NO: 15)
```

These peptides have been experimentally confirmed to exert the desired effect in the course of the present invention and thus provide a broad exemplary basis of the claimed invention.

In a further preferred embodiment, the peptide of the invention is fused to a further peptide or a polypeptide.

By fusing the peptide of the present invention to a further peptide or polypeptide, a fusion peptide or polypeptide is formed, i.e. an at least bipartite molecule comprising the peptide of the invention. The fusion peptide or polypeptide may exceed the length for a peptide as defined above, i.e. form an amino acid sequence of more than 30 amino acids which is defined as a polypeptide in accordance with the present invention which term is interchangeably used with the term "protein". Preferably, the further peptide does not have antimicrobial or antiviral activity. Alternatively, the further peptide displays antimicrobial or antiviral activity. Thus, it is conceivable in accordance with the present invention that two inventive peptides form said fusion peptide or fusion polypeptide. What is excluded by the term "fusion peptide" (or "fusion polypeptide") is that the sequence of the peptide of the present invention is simply extended N- and/or C-terminally by one or a few amino acids that do not confer any distinct function.

The fusion peptide or polypeptide of the present invention can be produced and isolated according to the methods described herein for the production of the peptide of the invention.

In a more preferred embodiment, the further peptide is a tag, a signal peptide, an antigenic determinant or a therapeutically active peptide such as a cytokine. Suitable polypeptides which can be fused to the peptide of the invention are polypeptides which may e.g. increase the solubility and/or facilitate the purification of the peptide of the invention.

The tag could serve for purification purposes if the peptide is produced by recombinant methods. Exemplary tags in this regard are a 6×His-tag, an HA-tag or a FLAG-tag which as such are known in the art. On the other hand, the tag could also be used to target the peptide of the invention to an organ or tissue wherein the cells express certain antigens to which the tag binds. Thus, the tag could e.g. be a peptide ligand for a receptor. Antigenic determinants allow for the purification of the fusion peptides via antibody affinity columns.

Signal peptides are short amino acid sequences capable of directing the peptide or protein to which they are attached to different cellular compartments or to the extracellular space (see e.g. Lusk et al., 2007 for signal peptides directing to the nucleus):

In a further more preferred embodiment, the peptide of the invention is fused to said further peptide or polypeptide via a linker.

A linker in connection with the present invention is used to connect the peptide of the invention with other peptides or with polypeptides. The linker serves to physically separate, the peptide of the invention and the other peptide or polypeptide and to ensure that neither the peptide of the invention nor the other peptide(s) or polypeptide(s) are limited in their function due to the close vicinity to each other. Depending on the other peptide or polypeptide, the linker can be a peptide bond, an amino acid, a peptide of appropriate length, or a different molecule providing the desired features. The skilled person knows how to design appropriate linker molecules, in particular linker peptides based on his/her common knowledge. For example, peptide linkers can be chosen from the LIP (Loops in Proteins) database (Michalsky et al., 2003). A linker may be appended to the N- or the C-terminus or, if deemed suitable, also to an amino acid apart from the terminal amino acids of the peptide of the present invention. The linker is preferably located at the N-terminus.

In a more preferred embodiment, the linker is a lysine, glycine, serine, an ether, ester or a disulphide.

In another embodiment, the present invention relates to a nucleic acid molecule encoding the peptide or the fused peptide (fused to another peptide or a polypeptide) of the invention.

The term "nucleic acid molecule" as used interchangeably with the term "polynucleotide", in accordance with the present invention, includes DNA, such as cDNA or genomic DNA, and RNA. Further included are nucleic acid mimicking molecules known in the art such as synthetic or semi-synthetic derivatives of DNA or RNA and mixed polymers. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (see Braasch and Corey, Chem Biol 2001, 8: 1). LNA is an RNA derivative in which the ribose ring is constrained by a methylene linkage between the 2'-oxygen and the 4'-carbon. They may contain additional non-natural or derivative nucleotide bases, as will be readily appreciated by those skilled in the art.

For the purposes of the present invention, also a peptide nucleic acid (PNA) can be applied. Peptide nucleic acids have a backbone composed of repeating N-(2-aminoethyl)-glycine units linked by peptide bonds. The purine and pyrimidine bases are linked to the backbone by methylene carbonyl bonds.

In a preferred embodiment, the nucleic acid molecule is DNA.

It will be readily appreciated by the skilled person that more than one nucleic acids may encode the peptide of the present invention due to the degeneracy of the genetic code. Degeneracy results because a triplet base code composed of four bases designates each of the 20 proteinogenic amino acids and a stop codon. The possible $4^3$ possibilities for bases in triplets gives 64 possible codons, meaning that some degeneracy must exist. As a result, some amino acids are encoded by more than one triplet, i.e. by up to six. The degeneracy mostly arises from alterations in the third position in a triplet. This means that nucleic acid molecules having a different sequences, but still encoding the same polypeptide lie within the scope of the present invention.

Further, the invention relates to an (expression) vector comprising the nucleic acid molecule of the invention.

Preferably, the a vector is a plasmid, cosmid, virus, bacteriophage or another vector used conventionally e.g. in genetic engineering.

The nucleic acid molecule of the present invention may be inserted into several commercially available vectors. Non-limiting examples include prokaryotic plasmid vectors, such as the pUC-series, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1 and vectors compatible with expression in mammalian cells like pREP (Invitrogen), pCEP4 (Invitrogen), pMC1neo (Stratagene), pXT1 (Stratagene), pSG5 (Stratagene), EBO-pSV2neo, pBPV-1, pdB-PVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogene), pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Invitrogen).

The nucleic acid molecule of the present invention referred to above may also be inserted into vectors such that a translational fusion with another nucleic acid molecule is generated. The other nucleic acid molecules may encode a protein which may e.g. increase the solubility and/or facilitate the purification of the protein encoded by the nucleic acid molecule of the invention. Non-limiting examples include pET32, pET41, pET43. Furthermore, the other nucleic acid molecule may encode a peptide or protein which enables for the compensation of the toxic properties of the antimicrobial peptides of the invention which would otherwise harm or kill the host cell (see below).

The vectors may also contain an additional expressible polynucleotide coding for one or more chaperones to facilitate correct protein folding. Suitable bacterial expression hosts comprise e. g. strains derived from BL21 (such as BL21 (DE3), BL21(DE3)PlysS, BL21(DE3)RIL, BL21(DE3) PRARE) or Rosetta®. For vector modification techniques, see Sambrook and Russel (2001). Generally, vectors can contain one or more origins of replication (ori) and inheritance systems for cloning or expression, one or more markers for selection in the host, e.g., antibiotic resistance, and one or more expression cassettes. Suitable origins of replication include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e. g., translation initiation codon, promoters, enhancers, and/or insulators), internal ribosomal entry sites (IRES) (Owens et al., 2001) and optionally poly-A signals ensuring termination of transcription and stabilization of the transcript. Additional regulatory elements may include transcriptional as well as translational enhancers, and/or naturally-associated or heterologous promoter regions. Preferably, the nucleic acid molecule of the invention is operably linked to such expression control sequences allowing expression in prokaryotes or eukaryotic cells. The vector may further comprise nucleotide sequences encoding signal peptides as further regulatory elements. Such sequences are well known to the person skilled in the art. Furthermore, depending on the expression system used, leader sequences capable of directing the expressed polypeptide to a cellular compartment may be added to the coding sequence of the nucleic acid molecule of the invention. Such leader sequences are well known in the art. Specifically-designed vectors allow the shuttling of DNA between different hosts, such as bacteria-fungal cells or bacteria-animal cells.

Preferably, the vector is an expression vector.

An expression vector according to this invention is capable of directing the replication, and the expression of the nucleic acid molecule of the invention and the peptide, fusion peptide or fusion polypeptide encoded thereby. Suitable expression vector are described above.

The nucleic acid molecules of the invention as described herein above may be designed for direct introduction or for introduction via liposomes, phage vectors or viral vectors (e.g. adenoviral, retroviral) into the cell. Additionally, baculoviral systems or systems based on Vaccinia Virus or Semliki Forest Virus can be used as vector in eukaryotic expression system for the nucleic acid molecules of the invention. Expression vectors derived from viruses such as retroviruses, vaccinia virus, adeno-associated virus, herpes viruses, or bovine papilloma virus, may be used for delivery of the polynucleotides or vector into targeted cell population. Methods which are well known to those skilled in the art can be used to construct recombinant viral vectors; see, for example, the techniques described in Sambrook, 2001 and Ausubel, 2001.

A typical (mammalian) expression vector contains the promoter element, which mediates the initiation of transcription of mRNA, the protein coding sequence, and signals required for the termination of transcription and optionally polyadenylation of the transcript. Moreover, elements such as origin of replication, drug resistance gene, regulators (as part of an inducible promoter) may also be included. Additional elements might include enhancers, Kozak sequences and intervening sequences flanked by donor and acceptor sites for RNA splicing. Highly efficient transcription and/or translation in mammalian cells can be achieved with the early and late promoters from SV40, the long terminal repeats (LTRs) from retroviruses, e.g., RSV, HTLVI, HIVI, and the early promoter of the cytomegalovirus (CMV). However, cellular elements and other viral promoters can also be used (e.g., the human actin promoter, chicken beta-actin promoter, CAG-promoter (a combination of chicken beta-actin promoter and cytomegalovirus immediate-early enhancer), the gai10 promoter, human elongation factor 1α-promoter, CMV enhancer, CaM-kinase promoter, the Autographa californica multiple nuclear polyhedrosis virus (AcMNPV), polyhedral promoter or a globin intron). Examples for regulatory elements permitting expression in yeast are the AOX1 or GAL1 promoter. The co-transfection with a selectable marker gene such as dhfr, gpt, G418, neomycin or hygromycin allows the identification and isolation of the transfected cells. The transfected nucleic acid can also be amplified to express large amounts of the encoded (poly)peptide. The DHFR (dihydrofolate reductase) marker is useful to develop cell lines that carry several hundred or even several thousand copies of the gene of interest. Another useful selection marker is the enzyme glutamine synthase (GS) (Murphy et al. 1991; Bebbington et al. 1992).

Using these markers, the mammalian cells are grown in selective medium and the cells with the highest resistance are selected. Suitable markers culturing in *E. coli* and other bacteria are tetracycline, kanamycin or ampicillin resistance genes for.

Possible regulatory elements permitting expression in prokaryotic host cells comprise, e.g., the lac, tip or tac promoter, the lacUV5 or the trp promoter in *E. coil*.

Besides elements which are responsible for the initiation of transcription, regulatory elements may also comprise transcription termination signals, such as the SV40-poly-A site or the tk-poly-A site or the SV40, lacZ and AcMNPV polyhedral polyadenylation signals, downstream of the polynucleotide.

The invention also relates to a host cell which may be grown in cell culture comprising the vector of the invention.

Suitable prokaryotic host cells comprise e.g. bacteria of the genera *Escherichia, Streptomyces, Salmonella* or *Bacillus*. It is of note that in case prokaryotic host cells are used, the vector of the invention preferably comprises the fusion peptide or fusion polypeptide of the invention if the expressed peptide alone would be toxic to said prokaryotic cells. This holds true in particular for those prokaryotic host cells which express LPS.

Suitable eukaryotic host cells are e.g. yeasts such as *Saccharomyces cerevisiae* or *Pichia pastoris*. Insect cells suitable for expression are e.g. *Drosophila* S2 or *Spodoptera* Sf9 cells. In order to be able to express the peptide of the invention in sufficient amounts, preferably the fusion peptide or the fusion polypeptide is encoded by the vector of the present invention if the expression of the peptide of the invention alone would be toxic to the host cell. This can easily be determined by the skilled person using routine biotechnological methods such as a test expression.

Mammalian host cells that could be used include, human Hela, HEK293, H9 and Jurkat cells, mouse NIH3T3 and C127 cells, COS 1, COS 7 and CV1, quail QC1-3 cells, mouse L cells, Bowes melanoma cells and Chinese hamster ovary (CHO) cells. Also within the scope of the present invention are primary mammalian cells or cell lines. Primary cells are cells which are directly obtained from an organism. Suitable primary cells are, for example, mouse embryonic fibroblasts (MEF), mouse primary hepatocytes, cardiomyocytes and neuronal cells as well as mouse muscle stem cells (satellite cells) and stable, immortalized cell lines derived thereof. Alternatively, the recombinant protein of the invention can be expressed in stable cell lines that contain the gene construct integrated into a chromosome.

Appropriate culture media and conditions for the above-described host cells are known in the art.

Alternatively, the host cell is an isolated cell. Such a cell has been isolated from a tissue of a multicellular organism or forms a protozoon. In the case of eukaryotic cells, the host cell of the present invention has been separated from the tissue where it is normally found. Cells found in cell culture, preferably in liquid cell culture, are isolated cells in accordance with the present invention.

As mentioned above, vectors of the present invention present or expressed in a host cell preferably comprise the nucleic acid molecule encoding the peptide of the present invention fused to a nucleic acid molecule encoding a peptide or polypeptide capable of compensating the potentially toxic effect of the peptide of the invention for the host cell if the peptide alone would be toxic to the cell.

In a further embodiment, the invention relates to a method of producing the peptide of the invention comprising culturing the host cell of the invention and collecting the peptide produced.

A large number of suitable methods exist in the art to produce peptides in appropriate hosts. If the host is a unicellular organism such as a prokaryote or a mammalian or insect cell, the person skilled in the art can revert to a variety of culture conditions. Conveniently, the produced protein is harvested from the culture medium, lysates of the cultured cells or from isolated (biological) membranes by established techniques. A preferred method involves the synthesis of nucleic acid sequences by PCR and their insertion into an expression vector. Subsequently a suitable host cell may be transfected or transformed etc. with the expression vector. Thereafter, the host cell is cultured to produce the desired peptide, which is isolated and purified.

Appropriate culture media and conditions for the above-described host cells are known in the art. For example, suitable conditions for culturing bacteria are growing them under aeration in Luria Bertani (LB) medium. To increase the yield and the solubility of the expression product, the medium can be buffered or supplemented with suitable additives known to enhance or facilitate both. *E. coli* can be cultured from 4 to about 37° C., the exact temperature or sequence of temperatures depends on the molecule to be overexpressed. In general, the skilled person is also aware that these conditions may have to be adapted to the needs of the host and the requirements of the peptide or protein expressed. In case an inducible promoter controls the nucleic acid of the invention in the vector present in the host cell, expression of the polypeptide can be induced by addition of an appropriate inducing agent. Suitable expression protocols and strategies are known to the skilled person.

Depending on the cell type and its specific requirements, mammalian cell culture can e.g. be carried out in RPMI or DMEM medium containing 10% (v/v) FCS, 2 mM L-glutamine and 100 U/ml penicillin/streptomycin. The cells can be kept at 37° C. in a 5% $CO_2$, water saturated atmosphere.

Suitable media for insect cell culture is e.g. TNM+10% FCS or SF900 medium. Insect cells are usually grown at 27° C. as adhesion or suspension culture. Suitable expression protocols for eukaryotic cells are well known to the skilled person and can be retrieved e.g. from in Sambrook, 2001.

As described above, when producing the peptide of the invention in a host cell, the expression vector preferably encodes a fusion peptide or fusion polypeptide if the peptide produced exerts toxic activity towards the host cell selected. This holds true in particular for bacteria producing LPS.

The fusion peptide or fusion polypeptide expressed has to be processed in order to cleave the compensating but undesired peptide or polypeptide fused to the peptide of the invention. This can take place at any stage of the purification process after culturing the host cell. Suitable methods to cleave off the undesired part are either chemical methods using e.g. cyanogen bromide which cleaves at methionine residues or N-chloro succinimide which cleaves at tryptophan residues. Alternatively, enzymatic methods can be used which are in general more gentle than chemical methods. Exemplary proteases suitable for cleavage are specific for a certain amino acid sequence and include Factor Xa or TEV protease.

An alternative method for producing the peptide of the invention is in vitro translation of mRNA. Suitable cell-free expression systems for use in accordance with the present invention include rabbit reticulocyte lysate, wheat germ extract, canine pancreatic microsomal membranes, *E. coli* S30 extract, and coupled transcription/translation systems such as the TNT-system (Promega). These systems allow the expression of recombinant peptides or proteins upon the addition of cloning vectors, DNA fragments, or RNA sequences containing coding regions and appropriate promoter elements.

Methods of isolation of the peptide produced are well-known in the art and comprise, without limitation, method steps such as ion exchange chromatography, gel filtration chromatography (size exclusion chromatography), affinity chromatography, high pressure liquid chromatography (HPLC), reversed phase HPLC, disc gel electrophoresis or immunoprecipitation (see, for example, Sambrook, 2001).

Furthermore, the invention relates to a pharmaceutical composition comprising the peptide or the fused peptide (i. e. the peptide of the invention fused to another peptide or a polypeptide) of the invention, the peptide or fused peptide produced by the method of the invention, the nucleic acid molecule of the invention, the expression vector of the invention or the host cell of the invention.

In accordance with the present invention, the term "pharmaceutical composition" relates to a composition for administration to a patient, preferably a human patient. The pharmaceutical composition of the invention preferably comprises the peptide of the invention. It may, optionally, comprise further molecules capable of altering the characteristics of the peptide of the invention thereby, for example, stabilizing, modulating and/or activating its function. The composition may be in solid, liquid or gaseous form and may be, inter alia, in the form of (a) powder(s), (a) tablet(s), (a) solution(s) or (an) aerosol(s). The pharmaceutical composition of the present invention may, optionally and additionally, comprise a pharmaceutically acceptable carrier. By "pharmaceutically acceptable carrier" is meant a non-toxic solid, semisolid or liquid filler, diluent, encapsulating material or formulation auxiliary of any type. Examples of suitable pharmaceutical carriers are well known in the art and include phosphate buffered saline solutions, water, emulsions, such as oil/water emulsions, various types of wetting agents, sterile solutions, organic solvents including DMSO etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgement of the ordinary clinician or physician. Generally, the regimen as a regular administration of the pharmaceutical composition should be in the range of 1 µg to 5 g units per day. However, a more preferred dosage might be in the range of 0.01 mg to 100 mg, even more preferably 0.01 mg to 50 mg and most preferably 0.01 mg to 10 mg per day.

The pharmaceutical composition of the present invention may be administered e.g. systemically, topically or parenterally. The term "parenteral" as used herein refers to modes of administration which include intravenous, intramuscular, intraperitoneal, intrasternal, subcutaneous and intraarticular injection and infusion.

In a further embodiment, the invention relates to the peptide or fused peptide of the invention, the nucleic acid molecule, the expression vector or the host cell of the invention, for treating infectious diseases, cancer or psoriasis.

An infectious disease is a clinically evident disease resulting from the presence of pathogenic microbial agents, including viruses, bacteria, fungi, protozoa, multicellular parasites, and aberrant proteins known as prions. These pathogens are able to cause disease in animals and/or plants.

Infectious pathologies are usually qualified as contagious diseases (also called communicable diseases) due to their potentiality of transmission from one person or species to another. Transmission of an infectious disease may occur through one or more of diverse pathways including physical contact with infected individuals. These infecting agents may also be transmitted through liquids, food, body fluids, contaminated objects, airborne inhalation, or through vector-borne spread.

Among the almost infinite varieties of microorganisms, relatively few cause disease in otherwise healthy individuals. Infectious disease results from the interplay between those few pathogens and the defenses of the hosts they infect. The appearance and severity of disease resulting from any pathogen depends upon the ability of that pathogen to damage the host as well as the ability of the host to resist the pathogen. Infectious microorganisms, or microbes, are therefore classified as either primary pathogens or as opportunistic pathogens according to the status of host defenses.

Primary pathogens cause disease as a result of their presence or activity within the normal, healthy host, and their intrinsic virulence (the severity of the disease they cause) is, in part, a necessary consequence of their need to reproduce and spread. Many of the most common primary pathogens of humans only infect humans, however many serious diseases are caused by organisms acquired from the environment or which infect non-human hosts.

One way of proving that a given disease is "infectious", is to satisfy Koch's postulates (first proposed by Robert Koch), which requires that the infectious agent be identified only in patients and not in healthy controls, and that patients who contract the agent also develop the disease. These postulates were first used in the discovery that *Mycobacteria* species cause tuberculosis. Koch's postulates cannot be assessed for ethical reasons for many human diseases because they require experimental infection of a healthy individual with a pathogen produced as a pure culture. Often, even diseases that are quite clearly infectious do not meet the infectious criteria. For example, *Treponema pallidum,* the causative spirochete of syphilis, cannot be cultured in vitro—however the organism can be cultured in rabbit testes. It is less clear that a pure culture comes from an animal source serving as host than it is when derived from microbes derived from plate culture. Epidemiology is another important tool used to study disease in a population. For infectious diseases it helps to determine if a disease outbreak is sporadic (occasional occurrence), endemic (regular cases often occurring in a region), epidemic (an unusually high number of cases in a region), or pandemic (a global epidemic).

Cancer, in accordance with the present invention refers to a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancers can, inter alia, be caused by pathogens such as viruses, e. g. cervical cancer caused by HPV.

In a more preferred embodiment, the infectious diseases are caused by bacterial infection.

Bacterial infections in accordance with the present invention include but are not limited to bacterial meningitis, cholera, diphtheria, listeriosis, pertussis (whooping cough), pneumococcal pneumonia, salmonellosis, tetanus, typhus or urinary tract infections. Included are also bacteria resistant to one or more commonly applied antibiotics, e.g. methicillin-resistant *Staphylococcus aureus* (MRSA).

In a further more preferred embodiment, the infectious disease is sepsis.

Sepsis is a serious medical condition characterized by a whole-body inflammatory state caused by infection.

Sepsis is broadly defined as the presence of various pathogenic organisms, or their toxins, in the blood or tissues. While the term sepsis is frequently used to refer to septicemia (blood poisoning), septicemia is only one type of sepsis. Bacteremia specifically refers to the presence of bacteria in the bloodstream (viremia and fungemia are analogous terms for viruses and fungi).

In addition to symptoms related to the provoking infection, sepsis is characterized by evidence of acute inflammation present throughout the entire body, and is therefore frequently associated with fever and elevated white blood cell count (leukocytosis). The modern concept of sepsis is that the host's immune response to the infection causes most of the symptoms of sepsis, resulting in hemodynamic consequences and damage to organs. This host response has been termed systemic inflammatory response syndrome (SIRS) and is characterized by hemodynamic compromise and resultant metabolic derangement.

This immunological response causes widespread activation of acute phase proteins, affecting the complement system and the coagulation pathways, which then cause damage to the vasculature as well as to the organs. Various neuroendocrine counter-regulatory systems are then activated as well, often compounding the problem. Even with immediate and aggressive treatment, this may progress to multiple organ dysfunction syndrome and eventually death.

In another more preferred embodiment, the infectious diseases are caused by viral infection.

Viral infections in accordance with the present invention include those caused by retroviruses such as alpha-, beta-, gamma- and deltaretroviruses (e. g. the human T-lymphotropic virus), spumaviruses, lentiviruses (e. g. the human immunodeficiency virus (HIV)), papilloma viruses such as HPV, hepatitis B and C viruses, and Herpes virus such as Epstein-Barr.

In addition, the present invention relates to a kit comprising the peptide of the invention, the peptide produced by the method of the invention, the nucleic acid molecule of the invention, the expression vector of the invention or the host cell of the invention.

The various components of the kit may be packaged in one or more containers such as one or more vials. The vials may, in addition to the components, comprise preservatives or buffers for storage.

The figures show:

FIG. 1:
Comparison of linear peptides Pep12, 17-1 and 19-1 to inhibit the LPS-induced cytokine expression in human mononuclear cells. The IPep19-1 inhibits most strongly the LPS-induced cytokine production.

FIG. 2:
The comparison of cyclic and linear peptides shows different secondary structures, obtained via the evaluation of the amide I-band of the peptide.

FIG. 3:
Binding of IPep19-2 to LPS measured by Isothermal Titration calorimetry.

FIG. 4:
Gel to liquid crystalline phase transition of the hydrocarbon chains of LPS in the presence of IPep19-2 (FIG. 4A) and IPep17-1 (FIG. 4B) from FTIR experiments.

FIG. 5:
Small-angle X-ray scattering (SAXS) patterns of LPS Ra:Pep19-2 mixtures at 20 and 50° C.

FIG. 6:
FRET experiments of labelled PS liposomes showing the intercalation of the peptide and peptide+LPS into the liposomes.

FIG. 7:
Action of some peptides against tumor cells (PC3=prostata carcinoma cells) as efflux of LDH (lactodehydrogenase)

FIG. 8:
Anti-HIV action of AMP's Pep19-2, -4, 6, and 8 at peptide concentrations of 1, 5, 10, and 20 µg/ml. The % inhibition of virus replication in a T-cell line is plotted versus peptide concentration showing an inhibition of 99% for peptides Pep19-5 and 19-8 at 20 µg/ml.

The examples illustrate the invention:

EXAMPLE 1

Peptide Synthesis

Linear peptides with the sequences described above were synthesized with an amidated C-terminus by the solid-phase peptide synthesis technique on an automatic peptide synthesizer on the standard Fmoc-amide resin according to the fastmoc synthesis protocol of the manufacturer. The N-terminal Fmoc-group was removed from the peptide-resin and the peptide was deprotected and cleaved with 90% trifluoroacetic acid (TFA), 5% anisole, 2% thioanisole, 3% dithiothreitol for 3 h at room temperature. After cleavage the suspension was filtered and the soluble peptides were precipitated with icecold diethylether followed by centrifugation and extensive washing with ether. Peptides were purified by RP-HPLC using an Aqua-C18 column (Phenomenex). Elution was done by using a gradient of 0-70% acetonitrile in 0.1% (TEA). The peptides were then again purified by reversed-phase HPLC to purities above 95%. Purity was determined by matrix-assisted laser-desorption-time-of-flight mass spectrometry (MALDI-TOF MS, Bruker).

EXAMPLE 2

Cytokine Secretion of Human Mononuclear Cells

Human mononuclear cells (MNC): heparinized (20 IU/ml) blood obtained from healthy donors was mixed with an equal volume of Hank's balanced solution, layered over Ficoll, and centrifuged for 40 min (21° C., 500 g). The interphase layer of MNC was collected and washed twice in Hank's medium and then resuspended in RPMI 1640 supplemented with 2 mM L-glutamine, 100 U/ml penicillin, and 100 µg/ml streptomycin. MNC (200 µl/well; 5×10$^6$ cells/ml) were transferred into 96-well culture plates. Twenty microliters of a mixture containing LPS (100 ng/ml or 10 ng/ml) and Gra-pep (10:1 weight % excess) was added to each well. Supernatants were harvested after 4 h incubation at 37° C. under 5% $CO_2$, and TNFα production was measured in a sandwich-ELISA. TNFα was determined in duplicate at two different dilutions and the values from two independent experiments were averaged.

EXAMPLE 3

Fourier-Transform Infrared Spectroscopy (FTIR)

For the infrared spectroscopic measurements, the lipid samples were placed in a $CaF_2$ cuvette with a 12.5 µM teflon spacer. Temperature-scans were performed automatically between 10 and 70° C. with a heating-rate of 0.6° C./min. Every 3° C., 50 interferograms were accumulated, apodized, Fourier transformed, and converted to absorbance spectra. For strong absorption bands, the band parameters (peak position, band width, and intensity) are evaluated from the original spectra, or after subtraction of the strong water bands if necessary. The main vibrational band used for the analysis is the symmetrical stretching vibration of the methylene groups $v_s(CH_2)$ located around 2850 cm$^{-1}$, a measure of order of the lipid A chains. For the determination of the secondary structures of the peptides, the amide I vibrational band in the range 1700 to 1600 cm$^{-1}$ is used.

EXAMPLE 4

Isothermal Titration Calorimetry (ITC)

Microcalorimetric measurements of peptide binding to the endotoxins were performed on a MCS isothermal titration calorimeter at 37° C. Briefly, after thorough degassing of the suspensions by ultrasonification, 1.5 ml of endotoxin samples (0.05 mM) were dispensed into the microcalorimetric cell, and 100 µl of peptide solutions (2 mM) were filled into the syringe compartment. After temperature equilibration, the peptides (3 µl) were titrated every 5 minutes into the lipid-containing cell under constant stirring. The heat of interaction measured by the ITC instrument after each injection was plotted versus time. The titration curves were repeated three times.

EXAMPLE 5

Small-Angle X-Ray Diffraction

X-ray diffraction measurements were performed at the European Molecular Biology Laboratory (EMBL) outstation at the Hamburg synchrotron radiation facility HASYLAB using the SAXS camera X33. Diffraction patterns in the range of the scattering vector $0.1<s<1.0$ nm$^{-1}$ ($s=2 \sin \theta/\lambda$, $2\theta$ scattering angle and $\lambda$ the wavelength=0.15 nm) were recorded at 40° C. with exposure times of 1 min using an image plate detector with online readout (MAR345, Mar-Research, Norderstedt/Germany). The s-axis was calibrated with Ag-behenate, which has a periodicity of 58.4 nm. The diffraction patterns can be evaluated by assigning the spacing ratios of the main scattering maxima to defined three-dimensional structures. The lamellar and cubic structures are the most relevant here. They are characterized by the following features:

(1) Lamellar: The reflections are grouped in equidistant ratios, i.e., 1, 1/2, 1/3, 1/4, etc. of the lamellar repeat distance dl;

(2) Cubic: The different space groups of these non-lamellar three-dimensional structures differ in the ratio of their spacings. The relation between reciprocal spacing shkl=1/dhkl and lattice constant a is $$s_{hkl}=[(h^2+k^2+l^2)/a]^{1/2}$$

(hkl=Miller indices of the corresponding set of plane).

FIG. 5 depicts small-angle X-ray scattering (SAXS) patterns of LPS Ra:Pep19-2 mixtures at 20 and 50° C. The small-angle X-ray scattering patterns obtained are characteristic for the existence of multilamellar aggregate structures of LPS, which is seen from the occurrence of reflections lying at equidistant ratios. Thus, at 20° C. one periodicity occurs at 9.71 with the second order reflection at 4.88 nm, another periodicity at 7.63 with the second order reflection at 3.84 nm and the main periodicity at 5.84 nm with two higher order reflections at 2.94 and 1.96 nm. The first periodicity corresponds to a nearly unaffected periodicity of pure LPS R60, whereas the two further periodicities with smaller values are indicative of strongly compressed lamellar stacks, from which the strongly reduced bioactivity of LPS becomes intelligible.

At 50° C., the periodicity of the undisturbed LPS disappears, and only the two multilamellar stacks with compressed lamellae remain.

EXAMPLE 6

Fluorescence Resonance Energy Transfer Spectroscopy (FRET)

Intercalation of the peptides and of LPS Re into liposomes was determined by FRET spectroscopy applied as a probe dilution assay. Liposomes were labelled with the donor dye NBD-phosphatidylethanolamine (NBD-PE) and acceptor dye Rhodamine-PE. Then, the lipids followed by peptides (or vice versa) were added to liposome at a final concentration of 1 µM. Intercalation was monitored as the increase of the ratio of the donor intensity ID at 531 nm to that of the acceptor intensity IA at 593 nm (FRET signal) in a time-dependent manner.

EXAMPLE 7

Antibacterial Activity of the Peptides

The antibacterial activity of the peptides was determined by microdilution susceptibility assays performed in Mueller-Hinton broth. Susceptibility testing was performed following the recommendations of the Clinical Standards Institute (CLSI, formerly NCCLS) [Standards, 2000]. Peptides (2 mg/ml in 4 mM HEPES, pH 7.2) were two-fold diluted in Mueller-Hinton Broth in 96-well microtitre plates to obtain concentrations from 512 to 0.25 µg/ml in a volume of 100 µl. Bacteria were grown on Mueller-Hinton agar plates for 1 to 3 days depending on the growth rate of the bacteria, suspended in 2 ml of 0.9% saline and adjusted to $10^8$ CFU/ml. The bacterial suspension was diluted 100-fold in Mueller-Hinton broth, and 0.1 ml of this new dilution ($10^5$ CFU) was added to the peptide dilutions. The microtiter plates were incubated at 37° C. for 24 h. The minimal inhibitory concentration (MIC) of each peptide against a given bacterial strain was regarded as the minimal concentration of the peptide which prevents the growth of that organism 24 h after inoculation. The bactericidal effect of the peptides was determined, after 24 h incubation at 37° C., by plating 10 µl of the content of non-cloudy wells onto Mueller-Hinton agar plates. Plates were incubated at 37° C. for 1 to 5 days, and a viable count was performed. The minimal bactericidal concentration (MBC) of each peptide for a given bacterial strain was regarded as the minimal concentration of the peptide which kills 99.9% of the colony-forming units (CFU) present in the final inoculum.

EXAMPLE 8

Animal Model of Endotoxicity

The wild-type LPS of *E. coli* ATCC 35218 and *P. aeruginosa* PAO1 were obtained from the aqueous phase of a water-phenol extract and purified by treatment with chaotropic agents and detergents.

Female ICR (CD-1) mice weighing 20-23 g were randomly distributed in experimental groups (n=16). Endotoxic shock was induced in the animals by coinoculation of LPS and galactosamine following the method of Galanos et al. Specifically, each animal received an intraperitoneal injection containing a mixture of 0.3 μg of LPS and 18 mg of galactosamine resuspended in 200 μl of endotoxin-free saline.

Immediately after LPS administration, animals were intraperitoneally inoculated with 150 μg of the test peptide resuspended in 150 μl of pyrogen-free saline containing 10% dimethylformamide as solubilizing agent. To facilitate the therapeutical action of the peptide, mice so treated were gently massaged at the site of inoculation for a few seconds. Animal mortality was monitored at 6 h and 12 h postinoculation and at daily intervals for 5 days.

In each independent experiment a group of animals received 150 μl of pyrogen-free saline containing 150 μg of polymyxin B, a lipopeptide with well known antiendotoxic properties, whereas another group was left untreated.

Results of animal mortality at all experimental time points were globally analyzed using the Kaplan-Meier survival analysis. When the survival plots were parallel, data were compared by the Log-Rank test, whereas for those plots that intersected the "Breslow-Gehan-Wilcoxon".

EXAMPLE 9

In animal experiments some peptides found in the course of the present invention were investigated, and so far three of the IPep19 series showed excellent activity, whereas the IPep17 series showed lower survival increase (see some examples in Table 1)

TABLE 1 antimicrobial activity of exemplary peptides in a mouse model

| Peptide | Dead mice/number of mice | | |
|---|---|---|---|
| | 24 h | 48 h | 72 h |
| LPS alone | 11/11 | | |
| LPS + PMB | 0/10 | 0/10 | 0/10 |
| LPS + I-Pep 17-1 | 7/11 | 7/11 | 8/11 |
| LPS + I-Pep 17-2 | 7/10 | 7/10 | 8/10 |
| LPS + I-Pep 19-2 | 0/10 | 0/10 | 0/10 |

It must be emphasized that the LPS dosage was very high (150 ng) in order to be able to observe clear effects. A dose reduction (50 ng/animal) was also performed. It could furthermore be shown that peptides of the 17-series was now much more effective (results not shown).

Furthermore, the ability of the peptides to inhibit the growth of relevant bacterial species was investigated:

The efficacy of the peptide of the present invention is shown on the three examples in table 2 below (in μg/ml):

TABLE 2

MIC and MBC values (duplicate determination) for a Gram-negative (E. coli), a Gram-positive (S. aureus) strain, and MIC values for two MRSA strains and the Gram-negative strains S. maltophilia and A. baumanii. MIC = minimal inhibition concentration, this is the concentration from which on no further growth is observed; MBC = minimal bactericidal concentration, the concentration, which not only inhibits bacterial growth but inactivated these completely.

| peptide | MIC | MIC | MBC | MBC |
|---|---|---|---|---|
| A) Escherichia coli ATCC 25922 | | | | |
| Pep 19-2 | 128 | 128 | 512 | 512 |
| Pep 19-4 | 15.6 | 7.8 | 15.6 | 15.6 |
| Pep 19-5 | 15.6 | 15.6 | 15.6 | 15.6 |
| Pep 19-6 | >500 | >500 | >500 | >500 |
| Pep 19-7 | >500 | >500 | >500 | >500 |
| B) Staphylococcus aureus ATCC 25923 | | | | |
| Pep 19-2 | 128 | 128 | 512 | 512 |
| Pep 19-4 | 15.6 | 15.6 | 62.5 | 125.0 |
| Pep 19-5 | 15.6 | 15.6 | 31.25 | 15.6 |
| Pep 19-6 | >500 | >500 | >500 | >500 |
| Pep 19-7 | >500 | >500 | >500 | >500 |

C) MRSA, S. maltophilia and A. baumanii

| | MRSA ATCC 43300 | MRSA CUN 3792-99 | Stenotrophomonas Maltophilia 3998-00 CUN | Acinetobacter baumanii ATCC 19606 |
|---|---|---|---|---|
| Pep19-2 | 128 | 1024 | 512 | 64 |
| Pep19-4 | 16 | 16 | 32 | 16 |
| Pep19-5 | 16 | 16 | 64 | 16 |
| Pep19-6 | 64 | 32 | 1024 | 64 |
| Pep19-7 | 16 | 16 | 645 | 16 |
| Pep18-8 | 8 | 8 | 32 | 16 |

EXAMPLE 10

The activity of some peptides according to the invention against tumor cells was tested by using PC3 (prostata carcinoma) cells. As measuring parameter the release of lactate hydrogenase was monitored which is connected with a reduction of NAD to NADH and thus indicates a damaging of the cells. The results of this experiment are depicted in FIG. 7. From FIG. 7, it can be seen that cell damage to the cancer cell line PC3 increases with increasing concentrations of peptide.

EXAMPLE 11

A T-cell line (PM1) was incubated with a HIV-1 isolate and the infected cells were cultivated in peptide-containing medium. After some days the number of viruses was determined as compared to untreated cells. The number of viruses is determined by the concentrations of the HIV-capsid in the supernatant.

FIG. 8 depicts the anti-HIV action of the peptides Pep19-2, -4, 6, and 8 at peptide concentrations of 1, 5, 10, and 20 μg/ml. The % inhibition of virus replication in a T-cell line is plotted versus peptide concentration showing an inhibition of 99% for peptides Pep19-5 and 19-8 at 20 μg/ml.

REFERENCES

1. Andersson, M. et al. (1996) NK-lysin, structure and function of a novel effector molecule of porcine T and NK cells. *Vet. Immuno. Immunopathol.* 54, 123-126
2. Andrä, J. et al. (2004) Biophysical characterization of the interaction of *Limulus polyphemus* endotoxin neutralizing protein with lipopolysaccharide. *Eur. J. Biochem.* 271, 2037-2046
3. Andrä, J. et al. (2007) Mechanism of interaction of optimized *Limulus*-derived cyclic peptides with endotoxins: thermodynamic, biophysical and microbiological analysis. *Biochem. J.* 406, 297-307

4. Andrä, J., et al. (2004) Biophysical characterization of endotoxin inactivation by NK-2, an antimicrobial peptide derived from mammalian NK-lysin. *Antimicrob. Agents Chemother.* 48, 1593-1599
5. Andrä, J. et al. (2004) Cyclic antimicrobial peptides based on *Limulus* anti-lipopolysaccharide factor for neutralization of lipopolysaccharide. *Biochem. Pharmacol.* 68, 1297-1307
6. Andrä, J. et al. (2007) Rationale for the design of shortened derivatives of the NK-lysin-derived antimicrobial peptide NK-2 with improved activity against Gram-negative pathogens. *J. Biol. Chem.* 282, 14719-14728
7. Brandenburg, K. (1993) Fourier transform infrared spectroscopy characterization of the lamellar and nonlamellar structures of free lipid A and Re lipopolysaccharides from *Salmonella minnesota* and *Escherichia coli. Biophys. J.* 64, 1215-1231.
8. Brandenburg, K. et al. (1999) Investigation into the acyl chain packing of endotoxins and phospholipids under near physiological conditions by WAXS and FTIR spectroscopy. *J. Struct. Biol.* 128, 175-186
9. Brandenburg, K. et al. (1990) Phase diagram of lipid A from *Salmonella minnesota* and *Escherichia coli* rough mutant lipopolysaccharide. *J. Struct. Biol.* 105, 11-21
10. Brandenburg, K. et al. (1992) Phase diagramm of deep rough mutant lipopolysaccharide from *Salmonella minnesota* R595. *J. Struct. Biol.* 108, 93-106
11. Brandenburg, K. et al. (1997) Conformational studies of synthetic lipid A analogues and partial structures by infrared spectroscopy. *Biochim. Biophys. Acta* 1329, 193-201
12. Brandenburg, K. et al. (2000) Physico-chemical characteristics of triacyl lipid A partial structure OM-174 in relation to biological activity. *Eur. J. Biochem.* 267, 3370-3377
13. Brandenburg, K. et al. (2002) Biophysical characterization of triacyl monosaccharide lipid A partial structures in relation to bioactivity. *Biophys. J.* 83, 322-333
14. Brandenburg, K. et al. (1993) Influence of the supramolecular structure of free lipid A on its biological activity. *Eur. J. Biochem.* 218, 555-563
15. Brandenburg, K. et al. (1998) Characterization of the nonlamellar cubic and $H_{II}$ structures of lipid A from *Salmonella enterica* serovar *Minnesota* by X-ray diffraction and freeze-fracture electron microscopy. *Chem. Phys. Lipids* 91, 53-69
16. Brandenburg, K. et al. (1996) Conformation of lipid A, the endotoxic center of bacterial lipopolysaccharide. *J. Endotoxin Res.* 3, 173-178
17. Brandenburg, K. and Wiese, A. (2004) Endotoxins: relationships between structure, function, and activity. *Curr. Top. Med. Chem.* 4, 1127-1146
18. Chen, X. et al. (2007) Biophysical analysis of the interaction of granulysin-derived peptides with enterobacterial endotoxins. *Biochim. Biophys. Acta* 1768, 2421-2431
19. Dankesreiter, S. et al. (2000) Synthetic endotoxin-binding peptides block endotoxin-triggered TNF-α production by macrophages in vitro and in vivo and prevent endotoxin-mediated toxic shock. *J. Immunol.* 164, 4804-4811
20. Garidel, P. et al. (2007) Novel antiinflammatory and anti-infective agents. *Antiinfective Agents Medic. Chem.* 6, 185-200
21. Hoess, A. et al. (1993) Crystal structure of an endotoxin-neutralizing protein from the horseshoe crab, *Limulus* anti-LPS factor, at 1.5 A resolution. *EMBO J.* 12, 3351-3356
22. Leslie, D. B. et al. (2006) Comparison of endotoxin antagonism of linear and cyclized peptides derived from *Limulus* anti-lipopolysaccharide factor. *Surg. Infect.* 7, 45-52
23. Mora, P. et al. (2006) Design of a minimized cyclic tetrapeptide that neutralizes bacterial endotoxins. *J. Pept. Sci.* 12, 491-496
24. Paus, E. J. et al. (2002) Production of recombinant endotoxin neutralizing protein in *Pichia pastoris* and methods for its purification. *Protein Expr. Purif* 26, 202-210
25. Ramamoorthy, A. et al. (2006) Cell selectivity correlates with membrane-specific interactions: a case study on the antimicrobial peptide G15 derived from granulysin. *Biochim. Biophys. Acta* 1758, 154-163
26. Ried, C., et al. (1996) High affinity endotoxin-binding and neutralizing peptides based on the crystal structure of recombinant *Limulus* anti-lipopolysaccharide factor. *J. Biol. Chem.* 271, 28120-28127
27. Vallespi, M. G. et al. (2003) A *Limulus* anti-LPS factor-derived peptide modulates cytokine gene expression and promotes resolution of bacterial acute infection in mice. *Int. Immunopharmacol.* 3, 247-256
28. Sambrook et al., "Molecular Cloning, A Laboratory Manual"; CSH Press, Cold Spring Harbor, 2001
29. Ausubel, "Current Protocols in Molecular Biology", Green Publishing Associates and Wiley Interscience, N.Y. (1989)
30. Lusk, C. P., Blobel, G., King, M. C. (2007). Highway to the inner nuclear membrane: rules for the road. *Nat Rev Mol Cell Biol.* 8(5):414-20.

The invention claimed is:

1. A peptide of linear, non-cyclic structure consisting of or comprising 17 to 23 amino acids, wherein the amino acids in positions 1 to 23, counted from the N-terminus, are as follows (1) G, S or lacking; (2) C or lacking; (3) K or R; (4) K or R; (5) Y, W or F; (6) K or R; (7) K or R; (8) F, W or L; (9) K or R; (10) K or L or lacking; (11) W, L or F; (12) K or R; (13) F, Y or C; (14) K or R; (15) G or Q; (16) K or R; (17) F, L or W; (18) F or W; (19) F, L or W; (20) W or F; (21) C or lacking; (22) F or G or lacking (23) G or lacking.

2. The peptide of claim 1, wherein said peptide comprises any one of the following amino acid sequences:

```
                                    (SEQ ID NO: 1)
lPep17-1:    KKFRRLKWKYKGKFWFW, (SEQ ID NO: 2)
lPep17-2:    KKYRRFRWKFKGKFWFW, (SEQ ID NO: 3)
lPep17-3:    RRYKKFKWRYRGRFWFW, (SEQ ID NO: 4)
lPep19-1:    GCKKFRRLKWKYKGKFWFWCG, (SEQ ID NO: 5)
lPep19-2:    GCKKYRRFRWKFKGKFWFWCG, (SEQ ID NO: 6)
lPep19-3:    GCRRYKKFKWRYRGRFWFWCG, (SEQ ID NO: 7)
lPep19-4:    GKKYRRFRWEFKGKWFWFG, (SEQ ID NO: 8)
lPep19-5:    GKKYRRFRWKFRGRFWFWG, (SEQ ID NO: 9)
lPep19-6:    GCKKFRRFKLKCKQKLWLWCG,
```

```
                       (SEQ ID NO: 10)
1Pep19-7:   GKKYRRFWKFKGKWFFWG, (SEQ ID NO: 11)
1Pep19-8:   GRRYKKFRWKFKGRWFWFG, (SEQ ID NO: 12)
1Pep19-9:   GCRRFKKFRWKYKGKFWFWCG, (SEQ ID NO: 13)
1Pep19-10:  GRRYKKFKWRFRGRFWFWG, (SEQ ID NO: 14)
1Pep19-11:  GCRRWKKFRWRYRGKFWFWCG
and (SEQ ID NO: 15)
1Pep19-12:  GCRRFKKFKKWRYRGRFWFWCFG.
```

3. The peptide of claim 1, wherein said peptide is fused to a further peptide or polypeptide.

4. The peptide of claim 3, wherein the further peptide is a tag, a signal peptide or an antigenic determinant.

5. The peptide of claim 3, wherein said peptide is fused to said further peptide or polypeptide via a linker.

6. A nucleic acid molecule encoding the peptide or fused peptide of claim 1 or 2 or said peptide fused to a further peptide or polypeptide.

7. An expression vector comprising the nucleic acid molecule of claim 6.

8. A host cell which may be grown in cell culture comprising the vector of claim 7.

9. A method of producing a peptide comprising culturing the host cell of claim 8 and collecting the peptide or fused peptide produced.

10. A pharmaceutical composition comprising the peptide of claim 1 or 2.

11. A method for treating an infectious disease comprising administering the peptide of claim 1 or 2 to a patient in need thereof, wherein the infectious diseases are caused by bacterial or HIV infection.

12. The method of claim 11, wherein the infectious disease is sepsis.

13. A method for treating prostate cancer comprising administering the peptide of claim 1 or 2 to a patient in need thereof.

14. The method of claim 11, wherein the infectious disease is caused by Gram negative bacteria.

* * * * *

UNITED STATES PATENT AND TRADEMARK OFFICE
CERTIFICATE OF CORRECTION

PATENT NO.       : 8,633,164 B2
APPLICATION NO. : 12/936976
DATED            : January 21, 2014
INVENTOR(S)      : Klaus Brandenburg It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 391 days.

Signed and Sealed this
Twenty-second Day of September, 2015

Michelle K. Lee
*Director of the United States Patent and Trademark Office*